United States Patent
Wollenberg et al.

(10) Patent No.: US 7,698,929 B2
(45) Date of Patent: Apr. 20, 2010

(54) HIGH THROUGHPUT SCREENING METHODS FOR LUBRICATING OIL COMPOSITIONS

(75) Inventors: Robert H. Wollenberg, Orinda, CA (US); Thomas J. Balk, San Francisco, CA (US)

(73) Assignee: Chevron Oronite Company, LLC, San Ramon, CA (US)

( * ) Notice: Subject to any disclaimer, the term of this patent is extended or adjusted under 35 U.S.C. 154(b) by 0 days.

(21) Appl. No.: 11/605,127

(22) Filed: Nov. 28, 2006

(65) Prior Publication Data

US 2007/0068228 A1    Mar. 29, 2007

Related U.S. Application Data

(62) Division of application No. 10/699,509, filed on Oct. 31, 2003, now Pat. No. 7,150,182.

(51) Int. Cl.
G01N 33/26    (2006.01)
(52) U.S. Cl. ...................... 73/53.05; 73/53.07
(58) Field of Classification Search ............... 73/53.05, 73/864.82, 864.85
See application file for complete search history.

(56) References Cited

U.S. PATENT DOCUMENTS

| | | | |
|---|---|---|---|
| 3,526,127 | A | 9/1970 | Sarkis |
| 4,209,414 | A | 6/1980 | Holgado et al. |
| 6,175,409 | B1 | 1/2001 | Nielsen et al. |
| 6,182,499 | B1 | 2/2001 | McFarland et al. |
| 6,187,164 | B1 | 2/2001 | Warren et al. |
| 6,235,691 | B1 | 5/2001 | Boffa et al. |
| 6,248,540 | B1 | 6/2001 | Weinberg et al. |
| 6,260,407 | B1 | 7/2001 | Petro et al. |
| 6,265,226 | B1 | 7/2001 | Petro et al. |
| 6,296,771 | B1 | 10/2001 | Miroslav |
| 6,326,090 | B1 | 12/2001 | Schultz et al. |
| 6,336,353 | B2 | 1/2002 | Matsiev et al. |
| 6,345,528 | B2 | 2/2002 | Petro et al. |
| 6,346,290 | B1 | 2/2002 | Schultz et al. |
| 6,371,640 | B1 | 4/2002 | Hajduk et al. |
| 6,373,570 | B1 | 4/2002 | McFarland et al. |
| 6,393,895 | B1 | 5/2002 | Matsiev et al. |
| 6,393,898 | B1 | 5/2002 | Hajduk et al. |
| 6,395,552 | B1 | 5/2002 | Borade et al. |
| 6,401,519 | B1 | 6/2002 | McFarland et al. |
| 6,406,632 | B1 | 6/2002 | Safir et al. |
| 6,410,331 | B1 | 6/2002 | Schultz et al. |
| 6,419,881 | B1 | 7/2002 | Weinberg et al. |

(Continued)

FOREIGN PATENT DOCUMENTS

WO    WO 02/07870    1/2002

*Primary Examiner*—Hezron Williams
*Assistant Examiner*—Mark Shabman
(74) *Attorney, Agent, or Firm*—Claude J. Caroli; M. Carmen & Associates PLLC (57) ABSTRACT

A method for determining storage stability for a plurality of fluid lubricant samples of different lubricating oil compositions is provided. Each sample includes a combination of one or more base oils and one or more lubricating oil additives. The methods can advantageously be optimized using combinatorial chemistry, in which a database of combinations of lubricating oil additives or lubricating oil compositions containing such additives is generated. As market conditions vary and/or product requirements or customer specifications change, conditions suitable for forming desired products can be identified with little or no downtime.

39 Claims, 5 Drawing Sheets

U.S. PATENT DOCUMENTS

| | | | |
|---|---|---|---|
| 6,420,179 | B1 | 7/2002 | Schultz et al. |
| 6,436,292 | B1 | 8/2002 | Petro |
| 6,438,497 | B1 | 8/2002 | Mansky et al. |
| 6,440,745 | B1 | 8/2002 | Weinberg et al. |
| 6,441,901 | B2 | 8/2002 | McFarland et al. |
| 6,461,515 | B1 | 10/2002 | Safir et al. |
| 6,468,806 | B1 | 10/2002 | McFarland et al. |
| 6,475,391 | B2 | 11/2002 | Safir et al. |
| 6,484,567 | B1 | 11/2002 | Hajduk et al. |
| 6,491,816 | B2 | 12/2002 | Petro |
| 6,508,984 | B1 | 1/2003 | Turner et al. |
| 6,519,032 | B1 | 2/2003 | Kuebler et al. |
| 6,528,026 | B2 | 3/2003 | Hajduk et al. |
| 6,535,284 | B1 | 3/2003 | Hajduk et al. |
| 6,535,824 | B1 | 3/2003 | Mansky et al. |
| 6,536,944 | B1 | 3/2003 | Archibald et al. |
| 6,541,259 | B1 * | 4/2003 | Lassner et al. ............... 435/468 |
| 6,541,271 | B1 | 4/2003 | McFarland et al. |
| 6,553,318 | B2 | 4/2003 | Mansky |
| 6,576,906 | B1 | 6/2003 | Archibald et al. |
| 6,577,392 | B1 | 6/2003 | Nielsen et al. |
| 6,582,116 | B2 | 6/2003 | Nielsen |
| 6,605,473 | B1 | 8/2003 | Hajduk et al. |
| 6,644,101 | B2 | 11/2003 | Hajduk et al. |
| 6,649,413 | B1 | 11/2003 | Schultz et al. |
| 6,650,102 | B2 | 11/2003 | Hajduk et al. |
| 6,653,138 | B1 | 11/2003 | Turner et al. |
| 6,655,194 | B2 | 12/2003 | Hajduk et al. |
| 6,658,429 | B2 | 12/2003 | Dorsett, Jr. |
| 6,664,067 | B1 | 12/2003 | Hajduk et al. |
| 6,668,622 | B2 | 12/2003 | Hajduk et al. |
| 6,670,298 | B1 | 12/2003 | Weinberg et al. |
| 6,679,130 | B2 | 1/2004 | Hajduk et al. |
| 6,681,618 | B2 | 1/2004 | Hajduk et al. |
| 6,686,205 | B1 | 2/2004 | Schultz et al. |
| 6,690,179 | B2 | 2/2004 | Hajduk et al. |
| 6,840,082 | B2 | 1/2005 | Evans |
| 2002/0023507 | A1 | 2/2002 | Hajduk et al. |
| 2002/0028456 | A1 | 3/2002 | Mansky et al. |
| 2002/0029621 | A1 | 3/2002 | Hajduk et al. |
| 2002/0032531 | A1 | 3/2002 | Mansky et al. |
| 2002/0098332 | A1 | 7/2002 | Warren et al. |
| 2002/0147116 | A1 | 10/2002 | Carrick et al. |
| 2002/0148282 | A1 | 10/2002 | Hajduk et al. |
| 2002/0155036 | A1 | 10/2002 | Hajduk et al. |
| 2002/0164275 | A1 | 11/2002 | Wheeler et al. |
| 2003/0007152 | A1 | 1/2003 | McFarland et al. |
| 2003/0032198 | A1 | 2/2003 | Lugmair et al. |
| 2003/0032205 | A1 | 2/2003 | McFarland et al. |
| 2003/0037601 | A1 | 2/2003 | Mansky et al. |
| 2003/0037620 | A1 | 2/2003 | Mansky |
| 2003/0041653 | A1 | 3/2003 | Matsiev et al. |
| 2003/0041671 | A1 | 3/2003 | Hajduk et al. |
| 2003/0041672 | A1 | 3/2003 | Hajduk et al. |
| 2003/0041676 | A1 | 3/2003 | Hajduk et al. |
| 2003/0054740 | A1 | 3/2003 | Mansky |
| 2003/0055587 | A1 | 3/2003 | Wang et al. |
| 2003/0056576 | A1 | 3/2003 | Mansky |
| 2003/0068829 | A1 | 4/2003 | Giaquinta et al. |
| 2003/0097871 | A1 | 5/2003 | Mansky |
| 2003/0100119 | A1 | 5/2003 | Weinberg et al. |
| 2003/0127776 | A1 | 7/2003 | Carlson et al. |
| 2003/0133113 | A1 | 7/2003 | Hajduk et al. |
| 2003/0138025 | A1 | 7/2003 | Archibald et al. |
| 2003/0141613 | A1 | 7/2003 | Hajduk et al. |
| 2003/0142309 | A1 | 7/2003 | Kuebler et al. |
| 2003/0157721 | A1 | 8/2003 | Turner et al. |
| 2003/0161763 | A1 | 8/2003 | Erden et al. |
| 2003/0169638 | A1 | 9/2003 | Nielsen |
| 2003/0190260 | A1 | 10/2003 | Wheeler et al. |
| 2003/0203500 | A1 | 10/2003 | Carlson et al. |
| 2003/0211016 | A1 | 11/2003 | Dales et al. |
| 2003/0218467 | A1 | 11/2003 | Carlson et al. |
| 2003/0219906 | A1 | 11/2003 | Giaquinta et al. |
| 2004/0123650 | A1 | 7/2004 | Kolosov et al. |

\* cited by examiner

HIGH THROUGHPUT SCREENING METHODS FOR LUBRICATING OIL COMPOSITIONS

PRIORITY

This application is a divisional of U.S. patent application Ser. No. 10/699,509, filed Oct. 31, 2003, now U.S. Pat. No. 7,150,182, the contents of which are incorporated herein by reference.

BACKGROUND OF THE INVENTION

1. Technical Field

The present invention relates generally to methods for high throughput screening of lubricating oil compositions.

2. Description of the Related Art

The use of a combinatorial approach for materials synthesis is a relatively new area of research aimed at using rapid synthesis and screening methods to build libraries of polymeric, inorganic or solid state materials. For example, advances in reactor technology have empowered chemists and engineers to rapidly produce large libraries of discrete organic molecules in the pursuit of new drug discovery, which have led to the development of a growing branch of research called combinatorial chemistry. Combinatorial chemistry generally refers to methods and materials for creating collections of diverse materials or compounds—commonly known as libraries—and to techniques and instruments for evaluating or screening libraries for desirable properties.

Presently, research in the lubricant industry involves forming candidate lubricating oil composition and then performing a macro-scale analysis of the formed composition. If the results of the test(s) are not satisfactory, the entire testing procedure will be repeated for a succession of individual candidate compositions, until one of the tested candidates will meet the required criterion. Typically, the methods employed for testing each candidate composition require manual operation. This, in turn, significantly reduces the number of compositions that can be tested and identified as leading lubricating oil compositions.

Ensuring proper function of lubricating oil compositions is critical to the successful operation and maintenance of mechanical systems, such as an automobile engine. Based on the current testing technique, as disclosed above, analysis of each oil composition candidate is time consuming and costly. Thus, it would be desirable to decrease the cost associated with the known testing procedures and to increase the efficiency thereof.

Additionally, changes in specifications and changing customer needs including new statutory requirements also drive reformulation efforts in other lubricant applications such as, for example, transmission fluids, hydraulic fluids, gear oils, marine cylinder oils, compressor oils, refrigeration lubricants and the like.

However, as stated above, present research in the lubricant industry does not allow for reformulation to occur in an expeditious manner. As such, there exists a need in the art for a more efficient, economical and systematic approach for the preparation of lubricating oil compositions and screening of such compositions for information correlating to the actual useful properties of the compositions.

Yet the availability of the complete data and efficient searching tool is critical to respond to, react to and even predict constantly changing new operating conditions and governmental and industrial standards or specifications. Thus, it would be invaluable if the data regarding a variety of diagnostic tests such as wear tests were complete and efficiently searched to design and select optimal lubricating oil compositions for applications such as diesel or internal combustion engines.

Accordingly, it would be desirable to rapidly test, classify and screen a plurality of sample candidate lubricating oil compositions utilizing small amounts to automatically determine and catalog anti-wear lubricating properties. In this manner, a high throughput screening of a vast number of diverse compositions can be achieved to select and identify leading lubricating oil compositions meeting specific anti-wear needs.

SUMMARY OF THE INVENTION

In accordance with one embodiment of the present invention, a high throughput screening method of lubricating oil compositions, under program control, is provided comprising the steps of:

(a) providing a plurality of different lubricating oil composition samples comprising (i) a major amount of at least one base oil of lubricating viscosity and (ii) a minor amount of at least one lubricating oil additive; (b) measuring wear stability of each sample to provide wear stability data for each sample; and, (c) outputting the results of step (b).

In accordance with another embodiment of the present invention, a high throughput screening method of lubricating oil compositions, under program control, is provided comprising the steps of (a) providing a plurality of different lubricating oil composition samples comprising (i) a major amount of at least one base oil of lubricating viscosity and (ii) a minor amount of at least one lubricating oil additive; (b) measuring extreme-pressure wear stability of each sample to provide extreme-pressure wear data for each sample; and, (c) outputting the results of step (b).

In a yet another embodiment of the present invention, a high throughput screening method of lubricating oil compositions, under program control, is provided comprising the steps of (a) providing a plurality of different lubricating oil composition samples comprising (i) a major amount of at least one base oil of lubricating viscosity and (ii) a minor amount of at least one lubricating oil additive; (b) measuring hydrodynamic wear stability of each sample to provide hydrodynamic wear data for each sample; and (c) outputting the results of step (b).

In yet a further embodiment of the present invention, a high throughput screening method of lubricating oil compositions, under program control, is provided comprising the steps of (a) providing a plurality of different lubricating oil composition samples comprising (i) a major amount of at least one base oil of lubricating viscosity and (ii) a minor amount of at least one lubricating oil additive; (b) measuring corrosive wear stability of each sample to provide corrosive wear data for each sample; and (c) outputting the results of step (b).

BRIEF DESCRIPTION OF THE DRAWINGS

The above and other features and advantages will become more readily apparent from the detailed description of the preferred embodiments of the present invention accompanied by the following drawings, in which.

DETAILED DESCRIPTION OF THE PREFERRED EMBODIMENTS

The present invention is directed to a high throughput screening method for determining lubricant performance of a plurality of different lubricating oil compositions by subjecting a plurality of different lubricating oil composition samples in a respective one of a plurality of test receptacles to measure wear stability. The expression "high throughput" as used herein shall be understood to mean that a relatively large number of different lubricating oil compositions are rapidly prepared and analyzed. In a first step of the screening method of the present invention, varying quantities of at least one base oil of lubricating viscosity and at least one lubricating oil additive are introduced in respective test reservoirs so that each reservoir contains a different lubricating oil composition having a different composition depending upon the percentage amounts and/or types of the additives combined with the base oil of lubricating viscosity in each receptacle. Data regarding the composition of each sample are stored in a data library. The procedure is advantageously accomplished under program control and is automatically controlled by, for example, a microprocessor or other computer control device. The expression "program control" as used herein shall be understood to mean the equipment used herein in providing the plurality of lubricating oil compositions is automated and controlled by a microprocessor or other computer control device.

The lubricating oil compositions for use in the high throughput screening method of this invention include as a first component a major amount of base oil of lubricating viscosity, e.g., an amount of greater than 50 wt. %, preferably greater than about 70 wt. %, more preferably from about 80 to about 99.5 wt. % and most preferably from about 85 to about 98 wt. %, based on the total weight of the composition. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both. The base oil for use herein can be any presently known or later-discovered base oil of lubricating viscosity used in formulating lubricating oil compositions for any and all such applications, e.g., engine oils, marine cylinder oils, functional fluids such as hydraulic oils, gear oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C.). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fischer-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500,etc.) or mono- and polycarboxylic esters thereof such as, for example, the acetic esters, mixed $C_3$-$C_8$ fatty acid esters, or the $C_{13}$oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methylhexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphonic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The second component of the lubricating oil compositions for use herein is at least one lubricating oil additive. Such additives can be any presently known or later-discovered additive used in formulating lubricating oil compositions. The lubricating oil additives for use herein include, but are not limited to, antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. Greases will require the addition of appropriate thickeners. A variety of the additives are known and commercially available. These additives, or their analogous compounds, can be employed for the preparation of the various lubricating oil compositions herein.

Alternatively, the lubricating oil additive(s) can further contain a diluent oil to form an additive concentrate. These concentrates usually include at least from about 90 wt. % to about 10 wt. % and preferably from about 90 wt. % to about 50 wt. %, of a diluent oil and from about 10 wt. % to about 90 wt. %, preferably from about 10 wt. % to about 50 wt. %, of the foregoing additive(s). Suitable diluents for the concentrates include any inert diluent, preferably an oil of lubricating viscosity such as, for example, a base oil as described hereinbelow, so that the concentrate may be readily mixed with lubricating oils to prepare lubricating oil compositions. Suitable lubricating oils that may be used as diluents can be any oil of lubricating viscosity.

Examples of antioxidants include, but are not limited to, aminic types, e.g., diphenylamine, phenyl-alpha-napthyl-amine, N,N-di(alkylphenyl) amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic) phenol; sulfur-containing materials, e.g., sulfurized olefins or esters and the like and mixtures thereof.

Examples of anti-wear agents include, but are not limited to, zinc dialkyldithiophosphates and zinc diaryldithiophosphates, e.g., those described in an article by Born et al. entitled "Relationship between Chemical Structure and Effectiveness of Some Metallic Dialkyl- and Diaryl-dithiophosphates in Different Lubricated Mechanisms", appearing in Lubrication Science 4-2 January 1992,see for example pages 97-100;aryl phosphates and phosphites, sulfur-containing esters, phosphosulfur compounds, metal or ash-free dithiocarbamates, xanthates, alkyl sulfides and the like and mixtures thereof.

Examples of detergents include, but are not limited to, overbased or neutral detergents such as sulfonate detergents, e.g., those made from alkyl benzene and fuming sulfuric acid; phenates (high overbased or low overbased), high overbased phenate stearates, phenolates, salicylates, phosphonates, thiophosphonates, ionic surfactants and the like and mixtures thereof. Low overbased metal sulfonates typically have a total base number (TBN) of from about 0 to about 30 and preferably from about 10 to about 25. Low overbased metal sulfonates and neutral metal sulfonates are well known in the art.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate;. stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$ fatty acid ester and a nitrogen-containing compound selected from the group consisting of ammonia, and an alkanolamine, e.g., those disclosed in U.S. Ser. No. 10/402,170, filed Mar. 28, 2003, the contents of which are incorporated by reference herein, and the like and mixtures thereof.

Examples of antifoaming agents include, but are not limited to, polymers of alkyl methacrylate; polymers of dimethylsilicone and the like and mixtures thereof.

Examples of ashless dispersants include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, phosphonoamides, thiophosphonamides and phosphoramides; thiazoles, e.g., 2,5-dimercapto-1,3,4-thiadiazoles, mercaptobenzothiazoles and derivatives thereof; triazoles, e.g., alkyltriazoles and benzotriazoles; copolymers which contain a carboxylate ester with one or more additional polar function, including amine, amide, imine, imide, hydroxyl, carboxyl, and the like, e.g., products prepared by copolymerization of long chain alkyl acrylates or methacrylates with monomers of the above function; and the like and mixtures thereof. The derivatives of these dispersants, e.g., borated dispersants such as borated succinimides, may also be used. Preferably, the dispersants are polyalkylene succinimides derived from animation of polyalkylene succinic anhydrides with polyalkylene polyamine.

If desired, prior to dispensing the at least one base oil and at least one lubricating oil additive to provide the compositions herein, as discussed hereinbelow, it can be advantageous to conduct molecular modeling of proposed compounds for use in the compositions (i.e., formulations) to determine which compounds may provide potential leading candidate compositions. For example, calculations can be carried out involving such factors as, for example, transition states, bond lengths, bond angles, dipole moment, hydrophobicity, etc, of the compounds. Accordingly, the proposed compounds can be screened to determine, for example, which compounds may perform poorly in an oxidation inhibition process due to a poor ability to trap intermediate peroxides. This can be carried out using known software such as, for example, Quantum Mechanics available from Accelrys (San Diego, Calif.).

Software for the design of test libraries can be used to design the original compound test libraries based on input from the foregoing experimental program(s). This software can be used to efficiently design test libraries that cover the desired experimental space and utilize statistical experimental design methods. Other software can then be used to analyze the data from the experiments and correlate that data with the structure of the compounds and/or compound treatment conditions and/or reaction conditions. Such correlations are often referred to as QSAR software (Quantitative Structure Activity Relations) available from Accelrys (San Diego, Calif.). Such QSAR programs can then be used by the software to design subsequent compound test libraries for further screening.

The use of such QSAR programs can add to the efficiency of screening. As more data is collected, these QSAR programs can become more efficient at developing compound libraries with increased probability for finding desirable compounds. For example, the compounds analyzed can be formulated into various lubricating oil compositions, as described herein, and then further analyzed by way of, for example, regression and analysis technologies, using known software, e.g., $C^2$-QSAR available from Accelrys (San Diego, Calif.). In this manner, validation of the data obtained from the molecular modeling can be achieved and then this data can also be stored in a data collector. In this way, new compounds, conceived by one skilled in the art can be checked by the QSAR software to predict their activity prior to their actual synthesis. Additionally, such software tools may be utilized to prioritize a list of possible compounds being considered for synthesis in such a way that one skilled in the art will have a higher probability for success.

Figure 1:
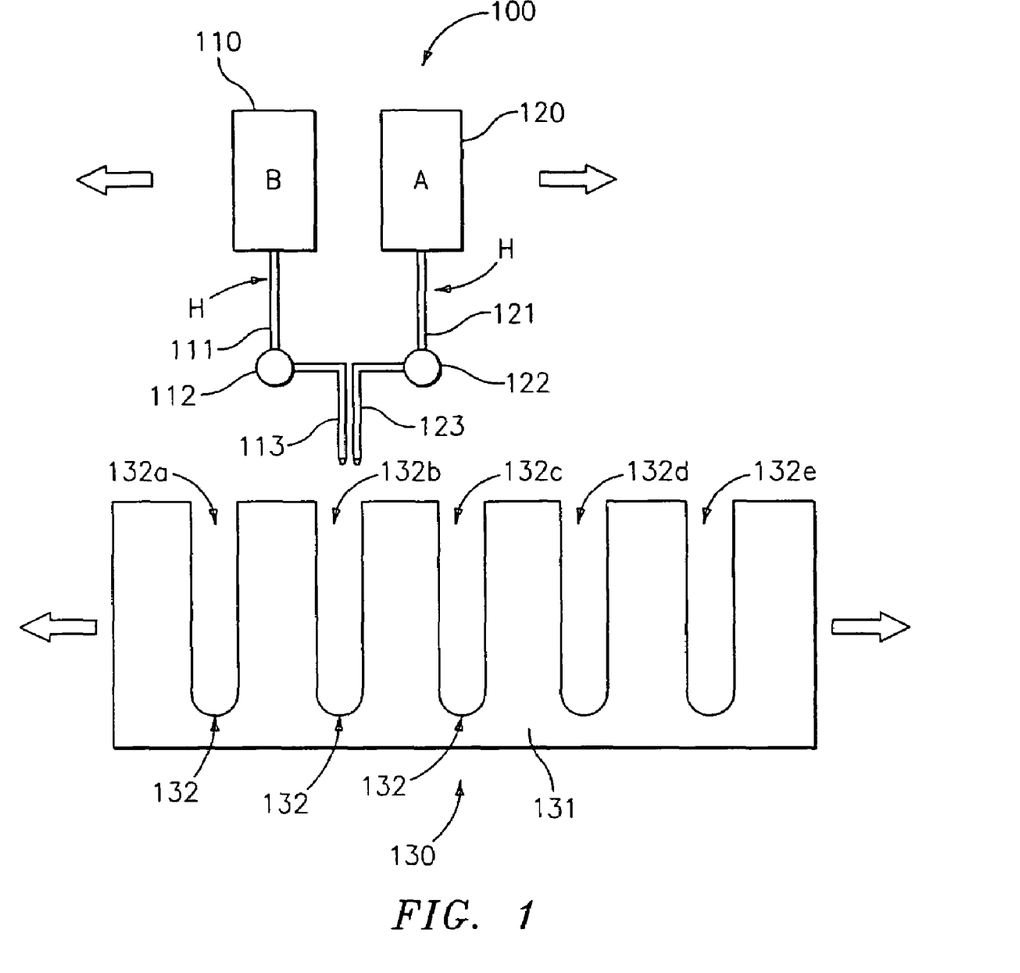
FIG. 1 is an example of the system of the present invention.

Referring now to FIG. 1, an example of a system to provide the foregoing compositions in the plurality of respective test receptacles is generally illustrated as system 100. Representative of this system and method for providing the foregoing compositions in the plurality of respective test receptacles is one disclosed in co-pending U.S. patent application Ser. No. 12/072,364 filed on Feb. 26, 2008 and entitled "HIGH THROUGHPUT PREPARATION OF LUBRICATING OIL COMPOSITIONS FOR COMBINATORIAL LIBRARIES" by Wollenberg et al. and having a common assignee with the present application, the contents of which are incorporated by reference herein. Generally, vessel 110 contains a supply of the foregoing base oils of lubricating viscosity B. Vessel 120 contains a supply of additive A, which can be any of the foregoing additives useful for modifying the properties of the base oil. As one skilled in the art would readily appreciate, one or more of vessels 110 and vessels 120 can be used when dispensing more than one base oil and/or more than one additive, respectively.

Tubular line 111 is a conduit for communicating the base oil B to nozzle portion 113, from which it can be dispensed into a selected test reservoir, as described below. The amount of base oil dispensed is determined by metering pump 112, which can be computer controlled.

Tubular line 121 is a conduit for communicating the lubricating oil additive A to nozzle portion 123, from which it can be dispensed into a selected test reservoir, as described below. The amount of lubricating oil additive dispensed is determined by metering pump 122, which also can be computer controlled. Computer programs and systems for automatically metering predetermined amounts of materials in accordance with a preselected protocol are known in the art and can be used herein.

Nozzles 113 and 123 are preferably in close proximity so that base oil B and additive A can be simultaneously dispensed in a test reservoir. Alternatively, base oil B and additive A can be sequentially added to the test reservoir. The nozzles 113 and 123 can comprise a multichannel pipette or one or more syringe needles.

The vessels 110 and 120 can be under pressure. Optionally, more than two vessels can be employed. Metering pumps suitable for use in the invention are known and commercially available. In the event that highly viscous lubricant base stock or additives are used, the vessels 110 and 120 and/or the tubular lines 111 and 121, metering pumps 112 and 122, and/or nozzles 113 and 123 can be heated to facilitate fluid flow therethrough.

The test frame 130 includes a block 131 of transparent material (e.g., glass) having a plurality of recesses 132 for receiving the dispensed additives or base oil and additives. The recesses provide test reservoirs wherein each reservoir contains lubricating oil additive compositions or lubricating oil compositions of a different and predetermined composition, i.e., the percentage and/or type of base oil and/or additives in each composition will vary from one reservoir to another. Optionally, the reservoirs can be individual receptacles (e.g., test tubes) mounted upon a rack, instead of being recesses in a block. Preferably, the test receptacles comprise transparent glass tubes. While five reservoirs, i.e., recesses 132*a*, 132*b*, 132*c*, 132*d*, 132*e*, are illustrated in FIG. 1, any number of reservoirs can be employed herein. For example the system can employ 20, 50, 100 or even more test receptacles and samples as required.

The individual reservoirs are adapted to hold relatively small amounts of samples. The sample size in each reservoir can generally be no more than about 20 ml, preferably no more than about 15 ml, more preferably no more than about 10 ml and yet more preferably no more than about 5 ml.

The test frame 130 and dispensing nozzles 113 and 123 are movable relative to one another. Although manual movement of the apparatus by an equipment operator is within the purview of the invention, robotic mechanisms with programmable movement are preferred. In one embodiment the test frame 130 is mounted upon a slidable carriage movable in a lateral and/or vertical direction so as to sequentially position a selected recess under the dispensing nozzles 113 and 123. In another embodiment, the nozzles 113 and 123, and optionally the vessels 110 and 120, are slidably movable laterally and/or vertically to accomplish positioning of the nozzles 113 and 123.

In a testing procedure, vessels 110 and 120 are filled with the selected lubricant base oil and additive(s), respectively. The apparatus of system 100 is moved such that dispensing nozzles 113 and 123 are positioned above and in alignment with recess 132*a*. A metered amount of base oil B and a metered amount of additive A are simultaneously dispensed into recess 132*a*. The dispensing nozzles 113 and 123 are thereafter repositioned to be in alignment with the next recess 132*b* and the metered amounts of additive A and/or base oil B are changed in accordance with a predetermined schedule of variation such that the lubricating oil in recess 132*b* has a different percentage composition of additive than that in recess 132*a*. The pattern is repeated as the nozzles 113 and 123 are sequentially aligned with the successive recesses 132*c*, 132*d*, and 132*e* so that each recess has a predetermined composition of lubricating oil.

The components A and B are preferably combined in the reservoirs by mixing, for example, by agitation of the frame 131, static mixing, individual stirring of the contents of the reservoirs (mechanical or magnetic stirring) and/or by bubbling the reservoir with gas, e.g., nitrogen. Optionally, base oil B and additive(s) A can be combined prior to dispensing into the respective reservoirs. For example, a single dispensing nozzle having a mixing chamber can be used, wherein base oil B and additive(s) A are metered into the mixing chamber and then dispensed through the nozzle into the reservoir.

Once the plurality of receptacles have been provided containing lubricating oil additive compositions and/or lubricating oil compositions, the plurality of fluid samples each can then be analyzed for respective anti-wear properties, i.e., wear stability. While classification of wear types includes, but are not limited to, adhesive wear, abrasive wear, fatigue, and polishing, the following are generally three major wear tests: extreme-pressure wear tests, hydrodynamic wear tests and corrosive wear tests.

An extreme-pressure wear test is associated with a situation where the lubricating oil composition has been squeezed out of the space between two rubbing surfaces, thereby leaving only a non-fluid film of anti-wear additive of the tested composition that has been chemically bonded to the interacting surfaces. For example, an extreme wear condition occurs between the piston ring and cylinder wall in a running internal combustion engine when the piston reaches the upper dead center and is subjected to the force of the fuel combustion explosion while the piston is for an instant not in sliding motion.

A hydrodynamic test is designed to test the ability of the lubricating oil compositions to prevent wear under conditions wherein a fluid lubricant film is retained between the interacting surfaces. Typically, a hydrodynamic lubricant condition occurs in an internal combustion engine between the piston rings and cylinder wall when the piston is in sliding motion during the stroke.

Finally, a corrosive wear test is designed to test the ability of the lubricating oil composition to protect the interacting surfaces from wear in a corrosive environment. The latter may be observed in an internal combustion engine due to the oxidation of components in the fuel or lubricating oil composition, e.g., in the case where sulfur generates sulfuric acid.

Figure 2:
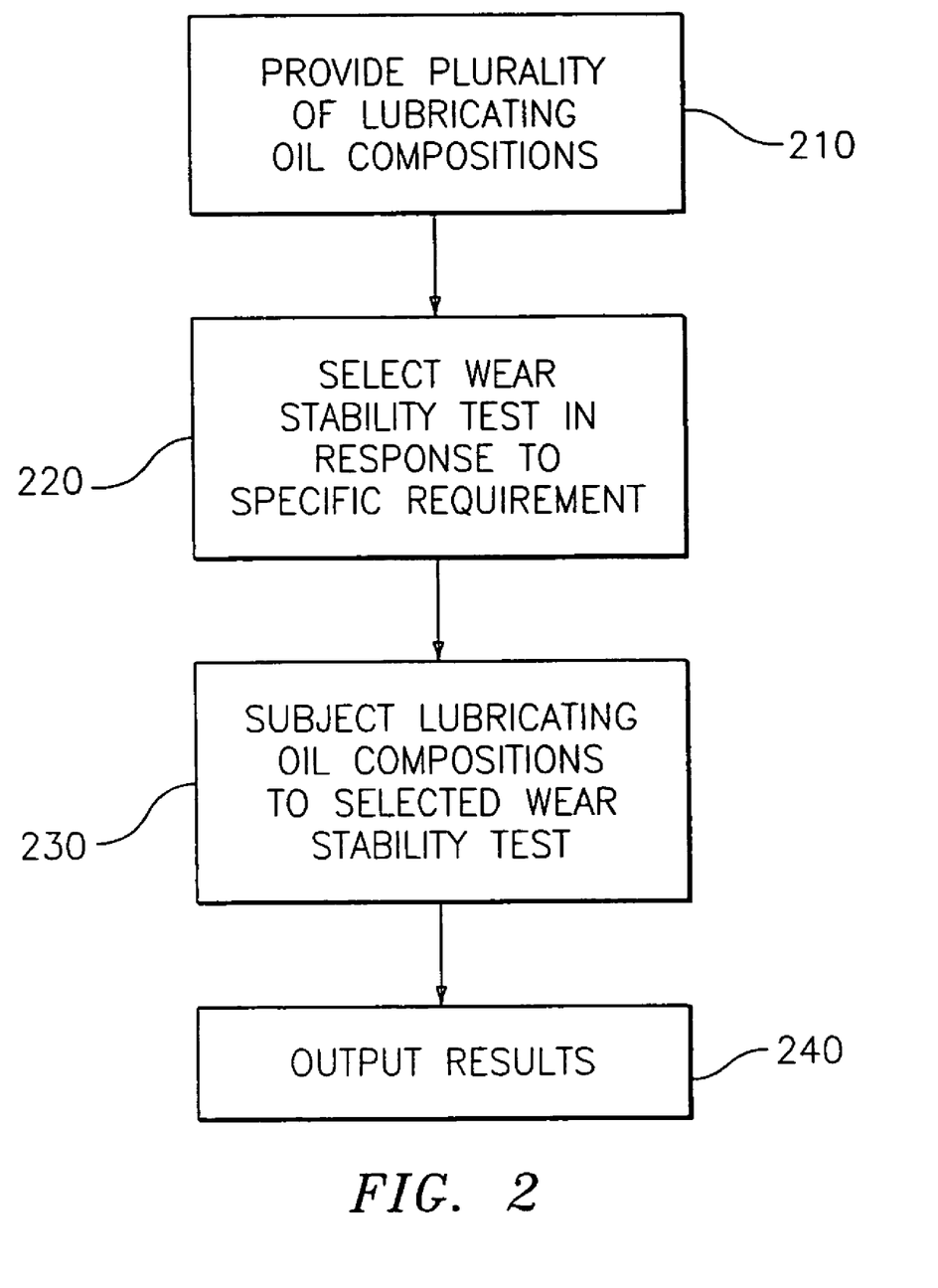
FIG. 2 is a flow chart of the method of the present invention for determining and storing anti-wear properties of a plurality of lubricating oil compositions provided in accordance with the system of FIG. 1.
Figure 3:
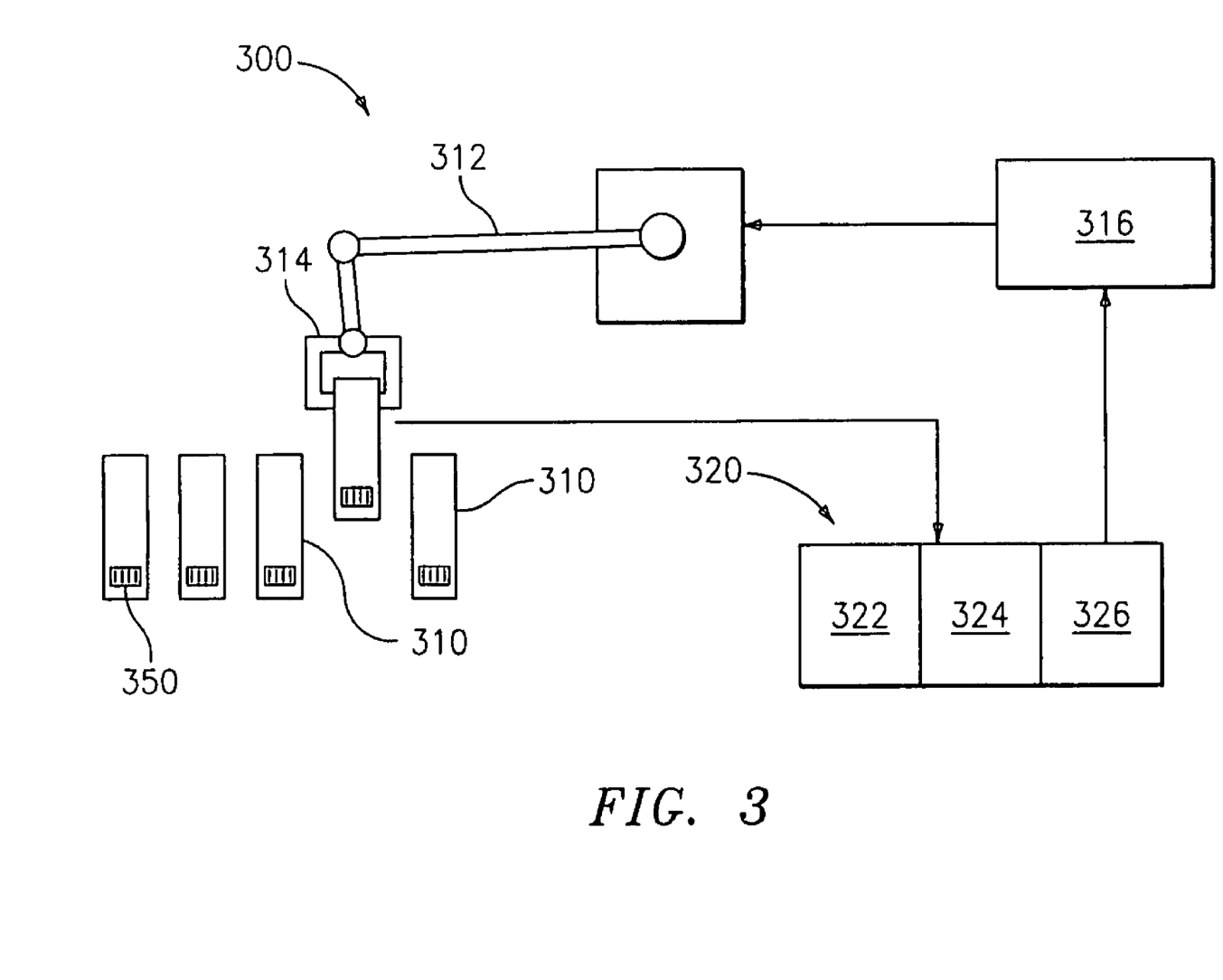
FIG. 3 is a diagrammatic view of an example of the system of the present invention capable of carrying out the method of FIG. 2.

Referring now to FIGS. 2 and 3, the method and system of the present invention for sequentially analyzing anti-wear properties of a plurality of lubricating oil compositions, stored in the library in accordance with FIG. 1, are illustrated. Adding the information related to the anti-wear properties of each of the stored lubricating oil compositions substantially facilitates the selection of candidate compositions capable of successfully carrying out the extreme-pressure, hydrodynamic and corrosive wear stability tests under the desired operating conditions or statutory requirements.

Having provided a plurality of lubricating oil compositions at 210 (FIG. 2), a robotic assembly 300 (FIG. 3) is adapted to carry out each of the tests by selectively delivering test receptacles 310, each containing a respective sample identifying code bar 350, to a testing station 320. The robotic assembly is configured to have one or more movable arms 312 each provided with a grasping mechanism 314, which engages the individual test receptacles 310 in accordance with instructions from a computer controller 316.

The testing station 320 may include a single testing apparatus performing one test at a time, or preferably, this station is assembled of multiple apparatuses operating simultaneously so that each carries out a respective test in accordance with instructions 220 (FIG. 2) from the controller 316. In case of multiple apparatuses, a tested lubricating oil composition can be distributed among an extreme pressure test apparatus 322, hydrodynamic test apparatus 324 and a corrosive test apparatus 326. Each of the test apparatuses operates under the desired and controlled conditions including, among others, a predetermined temperature, load and acid concentration corresponding to those specified in existing or proposed statutory requirements and corresponding to multiple parts of or the entire running engine. Thus, for example, the extreme pressure test apparatus 322 may operate so that the applied load sequentially increases in a time controlled manner from, for example, about 200 lbs. to about 300 lbs. to about 400 lbs. The hydrodynamic test apparatus 324 may be controlled to increase the load from, for example, about 50 lbs. to about 100 lbs. to about 150 lbs at intervals identical to or different from the intervals associated with the load increase in the extreme load apparatus 324. Finally, a corrosive element such as, for example, sulfuric acid, can be delivered in computer-controlled concentrations to the corrosive test apparatus 326 to recreate the desired corrosive environment corresponding to predetermined loads and acid concentrations to determine the corrosive wear stability of the lubricating oil composition. It is to be understood that the specific load and acid concentration conditions are not the only parameters that can be controllably created and modified in association with each of the test apparatuses.

As each of the lubricating oil compositions or a subset thereof is subjected to the foregoing test(s), as indicated by 230 of FIG. 2, the computer controller 316 (FIG. 3) processes and outputs respective test results at 240, each of which is added to the library. Accordingly, the information regarding the anti-wear properties of lubricating oil compositions stored in the library becomes another piece of information in addition to, for example, storage stability and oxidation stability of the cataloged compositions.

Figure 4:
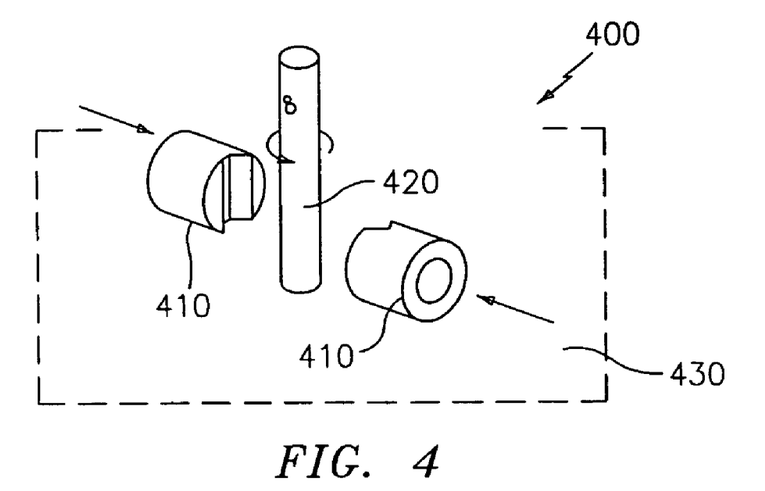
FIG. 4 is an exploded view of a Test Pin and Vee Block shown as an example of machinery capable of carrying out a plurality of wear tests in accordance with the method and system of the present invention.
Figure 5:
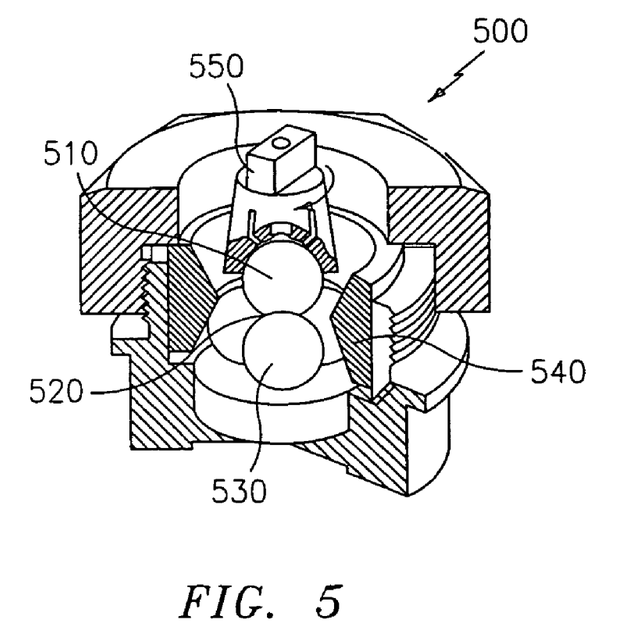
FIG. 5 is an isometric view of a Four-Ball Block Test 500 shown as another example of machinery capable of carrying out a plurality of wear tests in accordance with the method and system of the present invention; and, FIG. 6 is a flow chart of another embodiment the inventive method of FIG. 2 for determining and storing anti-wear properties of a plurality of lubricating oil compositions.

A variety of lubricant and wear testing machines or apparatuses are known to carry out the above-discussed tests. For example, as illustrated in FIGS. 4 and 5, Test Pin and Vee Block 400 and Four-Ball Test 500 assemblies, respectively, each are capable of performing the extreme pressure, hydrodynamic and corrosive wear tests either individually or in combination. For example, in the Test Pin configuration of FIG. 4, two Vee Blocks 410 can be controllably pressed against a rotating journal 420, which is submerged in a cup 430 with the tested lubricating oil composition. Accordingly, the hydrodynamic and extreme pressure tests for each of the lubricating oil compositions can be conducted sequentially by controllably increasing load. The corrosive test can be carried out simultaneously with or separately from each of the former two tests by delivering measured concentrations of an oxidation medium to the journal. Such delivery can be realized, for instance, by constantly injecting sulfuric acid at the point of the journal. Of course, the wear and/or rate of ware increase as the acid concentration increases.

The four-ball test configuration 500, as shown in FIG. 5, is constructed so that the three bottom test balls 530 are placed in a stationary holder 540, locked in place, and covered with a respective one of the lubricating oil compositions 520. Upon placing a top ball 510 in a chuck and attaching the top ball 510 to a spindle 550, the load is applied in a computer-controlled manner, as discussed above. Depending on which of the hydrodynamic and extreme pressure tests is being run, it is possible to determine either the load wear index corresponding to the scar diameter from the tests run or the weld point.

Figure 6:
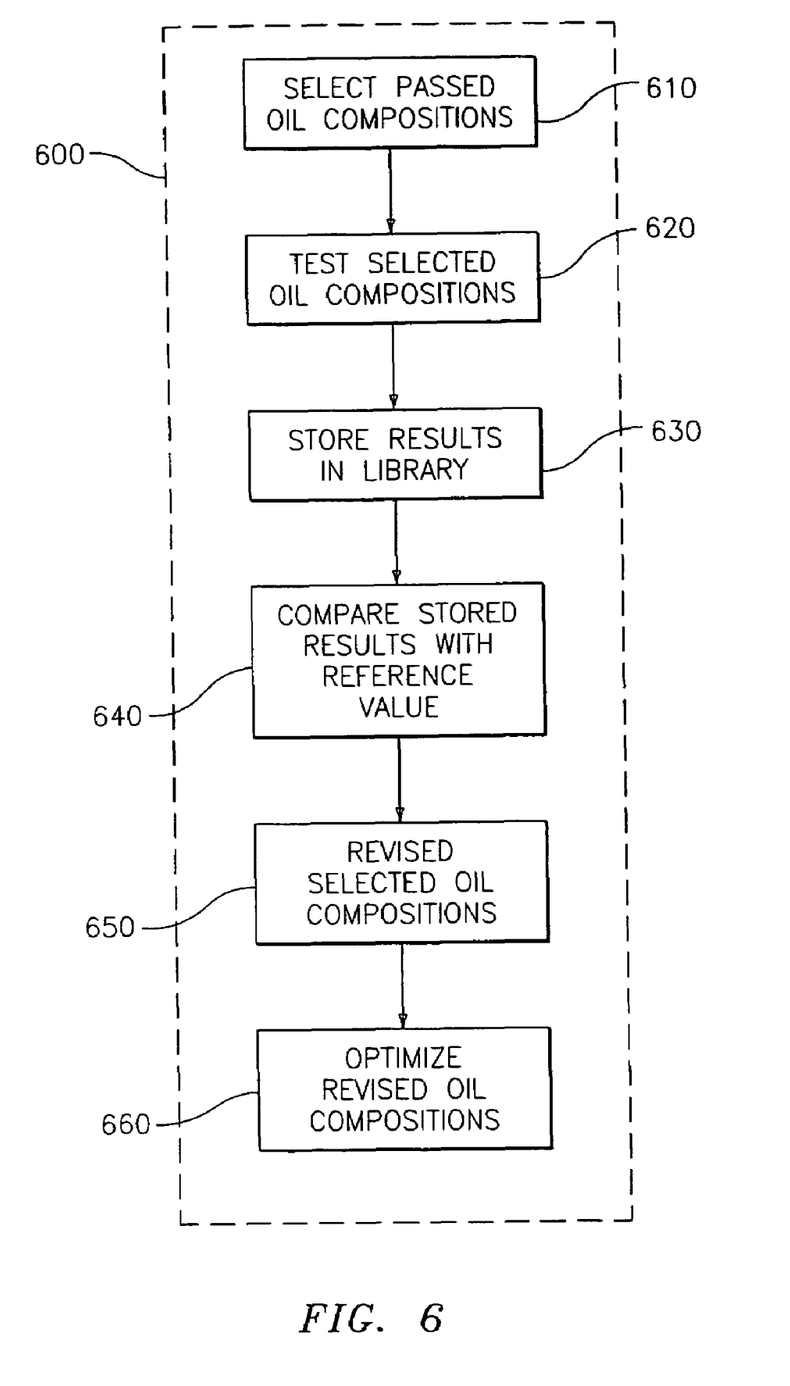

A particularly advantageous embodiment of a method and system of the present invention is illustrated in FIG. 6 and allows for rapid selection of those lubricating oil compositions cataloged in the electronic library that have anti-wear properties most suited for expected operating conditions or new statutory requirements. To realize such a selection, a computer controller 600 is operative to exclude those compositions that have been designated as failed to meet previous most stringent requirements and to select only the compositions with anti-wear characteristics that have been designated as passed, generally denoted at 610. The selected group may be tested again at 620 in accordance with the current requirements, including, for example, higher loads and/or temperatures or greater time of operation. The results of the test(s) can be transmitted and stored in the electronic library, as shown by step 630, and further be electronically compared to the expected results at 640. Following the comparison step, the selected group is revised at 650 and further narrowed to optimal candidates that exhibit the most appropriate anti-wear characteristics.

However, the use of the most suitable lubricating oil compositions for any given requirements may be associated with prohibitively high costs. In accordance with step 660, the method and system of the present invention enables the optimization of the selected candidates. The optimization of the selected lubricating oil compositions is the selection of the type and the amount of additive(s), which would provide a satisfactory, not necessarily the best, lubricating oil composition at the least cost. In other words, the optimization is a balancing test including performance and cost analysis based on the information stored in the electronic library in accordance with the method and system described herein.

In practical terms, it is necessary to keep in mind that each of the above-discussed tests simulates different parts of an actual mechanical system, such as a running engine. As a result, it can be found from the stored data that a given additive or oil composition is effective when used in a particular test by exhibiting a very steep slope response. As a consequence, adding the at least one additive to the at least one base oil in a small amounts can form a lubricating oil composition meeting new requirements. Furthermore, once again, tracing the slope responses of different additives, one can find that, for example, many additives while being effective for one type of the above-discussed tests do not produce encouraging results when used for other tests. Storing this information in the electronic library not only allows for a rapid selection of multiple lubricating oil compositions in response to new requirements for a given test, but also this information may allow for calculating necessary changes of the additives at the least cost.

For example, wear stability data regarding the lubricating oil compositions can be stored in a relational database to provide a combinatorial lubricating oil composition library. Alternatively, the system may be electrically connected to a signal data collector comprising a computer microprocessor for system operation and control to collect the data from the various tests over an extended period of time to compile the combinatorial lubricating oil composition library. The database can be used to find optimum combinations for a desired product stream, and can be particularly useful when the desired product stream varies depending on market factors. When the product requirements change, appropriate combinations can be selected to prepare the desired product.

Relational database software can be used to correlate the identity of the lubricating oil compositions and the analytical oxidation stability data obtained therefrom. Numerous commercially available relational database software programs are available, for example, from Oracle, Tripos, MDL, Oxford Molecular ("Chemical Design"), IDBS ("Activity Base"), and other software vendors.

Relational database software is a preferred type of software for managing the data obtained during the methods described herein. However, any software that is able to create a "memory map" of the lubricating oil compositions and correlate that information with the information obtained from the storage stability measurements can be used. This type of software is well known to those of skill in the art.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A high throughput system for screening a plurality of lubricating oil compositions, comprising:
 a) a supply of a major amount of at least one base oil of lubricating viscosity;
 b) a supply of a minor amount of at least one lubricating oil additive;
 c) a plurality of test receptacles;
 d) means for conducting molecular modeling of the at least one base oil of lubricating viscosity and the at least one lubricating oil additive to provide leading candidates of the at least one base oil of lubricating viscosity and at least one lubricating oil additive for combination to formulate a leading candidate lubricating oil composition for testing;
 e) means for combining selected quantities of the major amount of the at least one leading base oil of lubricating viscosity candidate with selected quantities of the minor amount of the at least one leading lubricating oil additive candidate in the plurality of test receptacles to form a plurality of leading candidate lubricating oil composition samples in the plurality of test receptacles;
 f) a moving unit configured to individually position each of the plurality of leading candidate lubricating oil composition samples in a testing station to test each of the leading candidate lubricating oil composition samples for wear stability and measure the wear stability of each test; and,
 g) a controller coupled to the testing station and configured to receive and store the measurements of the wear stability tests of each of the plurality of leading candidate lubricating oil composition samples.

2. The system of claim 1, wherein the controller is provided with software for automatically receiving and storing the measurements of wear stability of each of the plurality of lubricating oil compositions.

3. The system of claim 2, wherein the controller is provided with software for assembling the stored measurements of wear stability of each of the plurality of leading candidate lubricating oil composition samples processed on the testing station in an electronic library.

4. The system of claim 3, wherein the testing station includes at least one apparatus configured to conduct at least one wear stability test for measuring the wear stability of each of the plurality of leading candidate lubricating oil composition samples.

5. The system of claim 4, wherein the at least one wear stability test is selected from the group consisting of an extreme pressure test, hydrodynamic test, corrosive test and a combination thereof, the at least one apparatus being coupled to the controller having software, which executes thereon for selectively changing a plurality of conditions for the at least one wear stability test, the plurality of conditions being selected from the group consisting of duration of the at least one wear stability test, load generated during the at least one wear stability test, acid amount delivered during the at least one wear stability test and a combination thereof.

6. The system of claim 5, further comprising at least one additional apparatus coupled to the controller and configured to conduct each of the extreme pressure, hydrodynamic and corrosive tests of the plurality of leading candidate lubricating oil composition samples.

7. The system of claim 6, wherein the at least one additional apparatus operates simultaneously with the at least one apparatus, the controller being provided with software operating thereon for controlling each of the simultaneously operating apparatuses so that each one of the apparatuses conducts a respective test selected from the group consisting of an extreme pressure, hydrodynamic and corrosive wear stability test.

8. The system of claim 7, wherein the simultaneously operating apparatuses each conduct a respective one of the extreme pressure, hydrodynamic and corrosive tests different from the test conducted on the other one of simultaneously operating apparatuses.

9. The system of claim 8, wherein one of the simultaneously operating apparatuses is configured to conduct the corrosive test simultaneously with one of the extreme pressure and hydrodynamic tests.

10. The system of claim 5, wherein the controller has software operating thereon for analyzing a rate of change of a result of each of the extreme pressure, hydrodynamic and corrosive tests of a respective one of the plurality of leading candidate lubricating oil composition samples to select multiple groups thereof, each of which includes the lubricating oil compositions better suited for a particular one of the extreme pressure, hydrodynamic and corrosive tests.

11. The system of claim 10, wherein the controller further has software operating thereon for optimizing each of the selected multiple groups by balancing a cost of each of leading candidate lubricating oil composition samples included in a respective one of the selected multiple groups and a respective wear-stability result of the each of the leading candidate lubricating oil composition samples of the selected group.

12. The system of claim 1, wherein the plurality of leading candidate lubricating oil composition samples each is contained in a respective test receptacle.

13. The system of claim 12, wherein the moving unit includes a robotic arm configured to grasp and deliver each of the test receptacles to the testing station.

14. The system of claim 12, wherein each test receptacle has a bar code affixed to an outer surface thereof.

15. The system of claim 1, wherein the leading base oil of lubricating viscosity candidate is a natural oil.

16. The system of claim 1, wherein the at least one leading lubricating oil additive candidate is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

17. The system of claim 1, wherein the at least one leading lubricating oil additive candidate is an anti-wear agent.

18. The system of claim 1, wherein the at least one wear stability test is selected from the group consisting of an extreme pressure test, hydrodynamic test, corrosive test and a combination thereof.

19. The system of claim 1, wherein the leading base oil of lubricating viscosity candidate is a synthetic oil.

20. A high throughput system for screening a plurality of lubricating oil compositions, under program control, comprising:
   (a) a plurality of test receptacles, each containing a different lubricating oil composition each comprising (i) a major amount of at least one base oil of lubricating viscosity and (ii) a minor amount of at least one lubricating oil additive;
   (b) a moving unit configured to individually position each of the plurality of lubricating oil compositions in a testing station to test each of the lubricating oil compositions for wear stability and measure the wear stability of each test, wherein the wear stability test is selected from the group consisting of an extreme pressure wear test, hydrodynamic wear test, corrosive wear test and a combination thereof; and,
   (c) a controller coupled to the testing station and configured to receive and store the measurements of each of the extreme pressure, hydrodynamic and corrosive wear tests of each of the plurality of lubricating oil compositions, thereby assembling a library of the outputted results associated with each of the plurality of lubricating oil compositions, wherein each one of the wear tests is selected to be indicative of performance of a selected part of or an entire running internal combustion engine; and comparing the outputted results of at least one of the extreme pressure, hydrodynamic and corrosive wear tests of the plurality of lubricating oil compositions to a stored reference value selected from desired operating conditions or statutory requirements in accordance with the program control, wherein the controller has software operating thereon for analyzing a rate of change of a result of each of the extreme pressure, hydrodynamic and corrosive tests of a respective one of the plurality of lubricating oil compositions to select multiple groups thereof, each of which includes the lubricating oil compositions better suited for a particular one of the extreme pressure, hydrodynamic and corrosive tests.

21. The system of claim 20, wherein the controller is provided with software for automatically receiving and storing the measurements of each of the extreme pressure, hydrodynamic and corrosive wear tests of each of the plurality of lubricating oil compositions.

22. The system of claim 21, wherein the controller is provided with software for assembling the stored measurements of each of the extreme pressure, hydrodynamic and corrosive wear tests of each of the plurality of lubricating oil compositions processed on the testing station in an electronic library.

23. The system of claim 22, wherein the testing station includes at least one apparatus configured to conduct at least one of the extreme pressure, hydrodynamic and corrosive wear tests for measuring the wear stability of each of the plurality of lubricating oil compositions.

24. The system of claim 21, wherein the at least one apparatus being coupled to the controller having software, which executes thereon for selectively changing a plurality of conditions for the at least one of the extreme pressure, hydrodynamic and corrosive wear tests, the plurality of conditions being selected from the group consisting of duration of the at least one wear stability test, load generated during the at least one wear stability test, acid amount delivered during the at least one wear stability test and a combination thereof.

25. The system of claim 24, further comprising at least one additional apparatus coupled to the controller and configured to conduct each of the extreme pressure, hydrodynamic and corrosive tests of the plurality of lubricating oil compositions.

26. The system of claim 25, wherein the at least one additional apparatus operates simultaneously with the at least one apparatus, the controller being provided with software operating thereon for controlling each of the simultaneously operating apparatuses so that each one of the apparatuses conducts a respective one of the extreme pressure, hydrodynamic and corrosive wear tests.

27. The system of claim 26, wherein the simultaneously operating apparatuses each conduct a respective one of the extreme pressure, hydrodynamic and corrosive tests different from the test conducted on the other one of simultaneously operating apparatuses.

28. The system of claim 27, wherein one of the simultaneously operating apparatuses is configured to conduct the corrosive test simultaneously with one of the extreme pressure and hydrodynamic tests.

29. The system of claim 20, wherein the base oil of lubricating viscosity is a natural or synthetic oil.

30. The system of claim 20, wherein the at least one lubricating oil additive is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

31. The system of claim 20, wherein the at least one lubricating oil additive is an anti-wear agent.

32. A high throughput system for screening a plurality of lubricating oil compositions, under program control, comprising:
   a) a supply of a major amount of at least one base oil of lubricating viscosity;
   b) a supply of a minor amount of at least one lubricating oil additive;
   c) a plurality of test receptacles;
   d) means for conducting molecular modeling of the at least one base oil of lubricating viscosity and the at least one lubricating oil additive to provide leading candidates of the at least one base oil of lubricating viscosity and at least one lubricating oil additive for combination to formulate a leading candidate lubricating oil composition for testing;
   e) means for combining selected quantities of the major amount of the at least one leading base oil of lubricating viscosity candidate with selected quantities of the minor amount of the at least one leading lubricating oil additive candidate in the plurality of test receptacles to form a plurality of leading candidate lubricating oil composition samples in the plurality of test receptacles;
   f) moving unit configured to individually position each of the plurality of lubricating oil compositions in a testing station to test of the leading candidate lubricating oil composition samples for wear stability and measure the wear stability of each test, wherein the wear stability test is selected from the group consisting of an extreme pressure wear test, hydrodynamic wear test, corrosive wear test and a combination thereof; and,
   g) a controller coupled to the testing station and configured to receive and store the measurements of each of the extreme pressure, hydrodynamic and corrosive wear tests of each of the plurality of lubricating oil compositions, thereby assembling a library of the outputted results associated with each of the plurality of leading candidate lubricating oil composition samples, wherein each one of the wear tests is selected to be indicative of performance of a selected part of or an entire running internal combustion engine; and further configured to analyze a change of the outputted results of each of the extreme pressure, hydrodynamic and corrosive wear stability tests stored in the library upon changing a plurality of conditions in accordance with the program control.

33. The system of claim 32, wherein the controller is provided with software for automatically receiving and storing the measurements of each of the extreme pressure, hydrodynamic and corrosive wear tests of each of the plurality of leading candidate lubricating oil composition samples.

34. The system of claim 33, wherein the controller is provided with software for assembling the stored measurements of each of the extreme pressure, hydrodynamic and corrosive wear tests of each of the plurality of leading candidate lubricating oil composition samples processed on the testing station in an electronic library.

35. The system of claim 32, wherein the testing station includes at least one apparatus configured to conduct at least one wear stability test for measuring the wear stability of each of the plurality of leading candidate lubricating oil composition samples.

36. The system of claim 32, wherein the controller is provided with software for selectively changing the plurality of conditions for the at least one of the wear test, the plurality of conditions being selected from the group consisting of duration of the at least one wear stability test, load generated during the at least one wear stability test, acid amount delivered during the at least one wear stability test and a combination thereof.

37. The system of claim 32, wherein the leading base oil of lubricating viscosity candidate is a natural or synthetic oil.

38. The system of claim 32, wherein the at least one leading lubricating oil additive candidate is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

39. The system of claim 32, wherein the at least one leading lubricating oil additive candidate is an anti-wear agent.

* * * * *